(12) United States Patent
Qian et al.

(10) Patent No.: US 6,429,021 B1
(45) Date of Patent: Aug. 6, 2002

(54) ANTIOXIDANT ACTIVITY PROFILE ASSAY

(75) Inventors: Yong Qian, San Diego; Richard E. A. Leitz, Hemet; David W. Krempin, Tumacula, all of CA (US)

(73) Assignee: Amway Corporation, Ada, MI (US)

( * ) Notice: Subject to any disclaimer, the term of this patent is extended or adjusted under 35 U.S.C. 154(b) by 0 days.

(21) Appl. No.: 09/044,573

(22) Filed: Mar. 19, 1998

(51) Int. Cl.[7] .................. G01N 30/90; G01N 30/94
(52) U.S. Cl. .................. 436/162; 436/127; 436/164; 436/178
(58) Field of Search .................. 436/161, 162, 436/127, 164, 178

(56) References Cited

U.S. PATENT DOCUMENTS

| | | |
|---|---|---|
| 4,253,848 A | 3/1981 | Porter |
| 5,239,258 A | 8/1993 | Kauffman |
| 5,427,951 A | 6/1995 | Davies et al. |
| 5,451,526 A | 9/1995 | Cui et al. |
| 5,556,787 A | 9/1996 | Miller |
| 5,753,697 A | * 5/1998 | Joyeux et al. |
| 5,762,836 A | * 6/1998 | Ronzio et al. |

FOREIGN PATENT DOCUMENTS

WO      95/01174    * 1/1995

OTHER PUBLICATIONS

"Acetone Powder Prep by Schleicher et al" at http://expmed.bwh.harvard.edu/protocols/acetone_powder.html (Oct. 15, 2001).*

Koelle, Michael, "Preabsorbing Antisera with C. elegans Acetone Powder" at http://info.med.yale.edu/mbb/koelle/protocols/protocol_Ab_preabsorbtion.html (Oct. 15, 2001).*

Cuendet et al., Helv. Chim. Acta (1997), 80(4), 1144–1152.*

Takao et al., Biosci. Biotechnol. Biochem. (1994), 58(10), 1780–1783.*

Finocchiaro et al., J. Assoc. Off. Anal. Chem. (1965), 48(4), 736–738.*

Finocchiaro et al., J. Assoc. Off. Anal. Chem. (1967), 50(4), 888–8963.*

Bors et al., Moderm Methods Plant Anal. New Ser. (1992), 13, 277–295.*

Chemical Abstract No. 127:202946, Cuendet et al., Helv. Chim. Acta (1997), 80(4), 1144–1152.*

Chemical Abstract No. 121:294516, Takao et al., Biosci. Biotechnol. Biochem. (1994), 58(10), 1780–1783.*

Chemical Abstract No. 74:13961, Kazarinova et al., Kauch. Rezina (1970), 29(9), 51–53.*

Chemical Abstract No. 67:81415, Finocchiaro et al., J. Assoc. Off. Anal. Chem. (1967), 50(4), 888–896.*

"Antioxidant Determination by the Use of a Stable Free Radical", *Nature*, Apr. 26, 1958, No. 4617, pp. 1199–1200.

"Scavenging Effect of Methanolic Extracts of Peanut Hulls on Free–Radical and Active–Oxygen Species", *J. Agric Food Chem.*, 1994, vol. 42, No. 3, pp. 629–932.

* cited by examiner

*Primary Examiner*—Jan Ludlow
(74) *Attorney, Agent, or Firm*—Brinks Hofer Gilson & Lione; G. Peter Nichols

(57) ABSTRACT

The present invention provides an assay for detecting the presence of an array or a profile of antioxidant activity in any sources or products. In particular, the invention provides a method in which a sample is extracted with a polar, a non-polar and a semi-polar solvent to obtain three extracts; the extracts are chromatographed to get a chemical profile; and the profile is analyzed to determine the presence of antioxidants by directly reacting to a free-radical.

11 Claims, 1 Drawing Sheet

ANTIOXIDANT ACTIVITY PROFILE ASSAY

The present invention provides an assay for detecting the presence of an array or a profile of antioxidant activity in any sources or products.

BACKGROUND OF THE INVENTION

When materials such as food are exposed to air, oxidative deterioration can occur. Oxidation can detrimentally effect the taste, color, and nutritional content of food. To prevent this deterioration, compounds that prevent oxidation, antioxidants, are added to food. Traditionally, the food industry has relied on antioxidants which are chemically synthesized. However, the possible toxicity of these compounds has stimulated the search for natural products with antioxidant properties. Similarly, a trend in the nutritional industry is to provide supplements providing antioxidant activity. These supplements are useful for eliminating free radicals that may contribute to aging or disease in mammals.

In the past, materials were screened for antioxidant activity using methods that determine the total antioxidant activity of all the antioxidants in the sample. For example, Yen and Duh, *J Agric. Food Chem.* 1994, 42:629–632, extracted peanut hulls with a polar solvent (methanol) and determined the total amount of antioxidant activity of all of the natural products contained in the extract. The ability of this mixture of compounds to scavenge each of a stable free radical, a peroxide, metals, superoxide, and hydroxyl radical was studied. However, their method was of limited use for two reasons. First, the antioxidant activity of all the natural products in the polar fraction are reported as a single total value. Unfortunately, from this report, one cannot ascertain the individual antioxidant activity of each natural product. Second, the antioxidant activity of the remaining fractions (the non-polar and semi-polar fractions) were not tested.

Similarly, others have also reported methods for determining the antioxidant activity of all the natural products in a sample. Kauffman, U.S. Pat. No. 5,239,258, describes a method in which a sample of material is dissolved and subjected to single sweep voltammetric analysis to measure the current through the sample as a function of the potential applied. The resulting current-voltage plot reflects the total level of oxidation products present in the material sampled. Davies, U.S. Pat. No. 5,427,951, describes a diagnostic test in which a sample is contacted with myoglobin and a compound which reacts to form a chromogenic species. Miller, U.S. Pat. No. 5,556,787, describes a method of determining the presence of oxidants or reductants in a sample using polyanilines as chromogenic agents. Porter, U.S. Pat. No. 4,253,848, describes a method for rapid, dry, non-destructive assay of the oxidative status of unsaturated lipids in whole foods, fats or oils by monitoring the fluorescence of compounds formed by the reaction of volatiles from oxidizing lipids and a polymerized ε-caprolactam. Like the method of Yen and Duh, the antioxidant activity of all the natural products in sample are reported as a single total value.

There is a need for a method that detects the antioxidant activity of individual antioxidants in a sample. Such a method would allow one to identify individual compounds with antioxidant activity, to monitor the stability of the antioxidant activity of individual components over time, and to compare the antioxidant profile of different samples.

SUMMARY OF THE INVENTION

The present invention provides a rapid and efficient method for identifying an antioxidant activity profile of a sample. Such a profile allows one to readily ascertain the total activity of the sample and to attribute antioxidant activity to individual components.

DETAILED DESCRIPTION OF THE INVENTION

Figure 1:
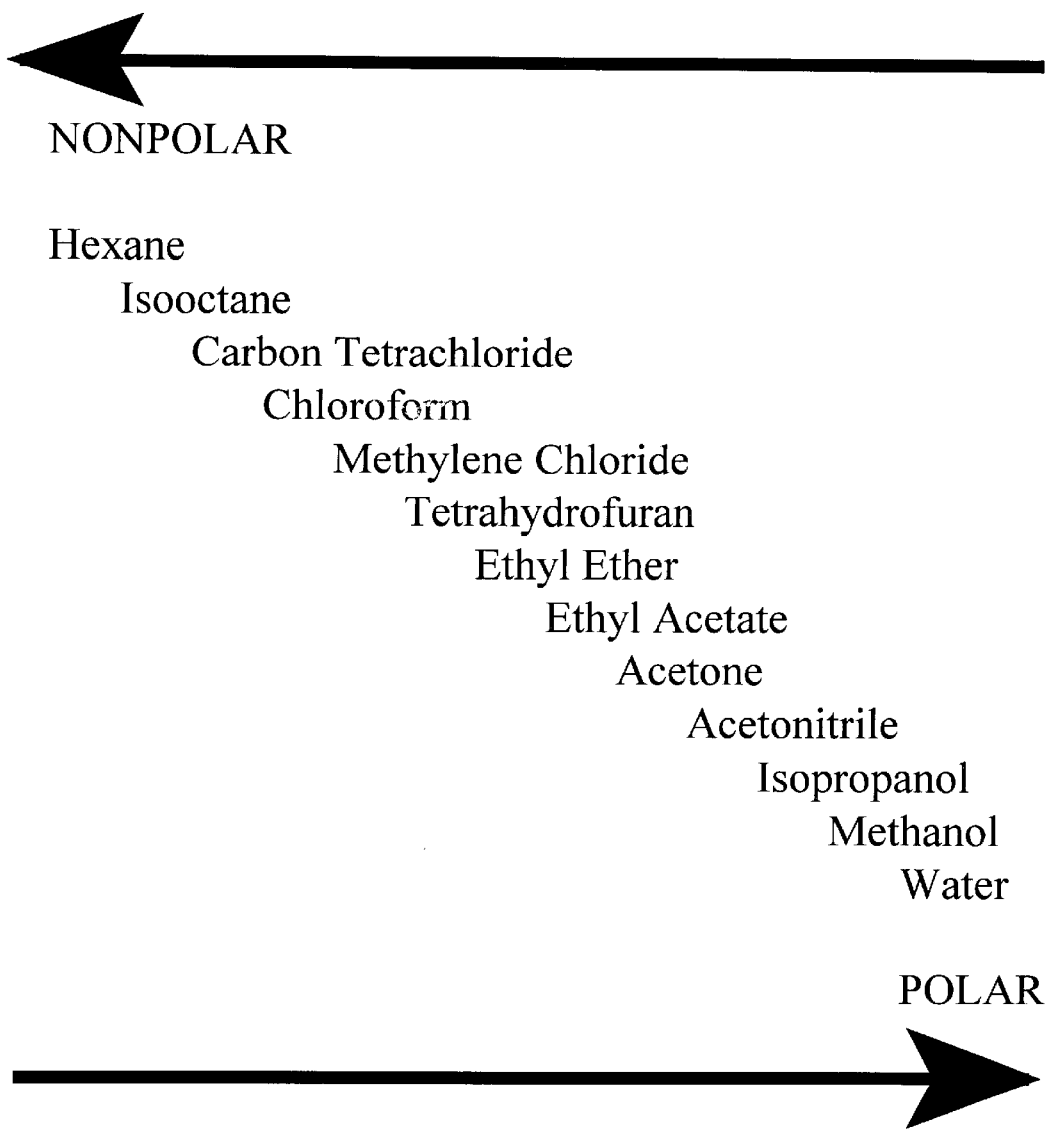
FIG. 1 shows a chart of various solvents and their relative polarities.

"Antioxidant" means a compound that is effective in retarding the oxidation of a molecule such as a lipid, lipoprotein, protein or DNA. In the present invention, antioxidants in a sample are classified into three major groups according to their chemical properties.

The invention provides a method of determining the antioxidant activity profile of a sample by extracting the sample with at least one polar solvent, at least one non-polar solvent and/or at least one semi-polar solvent to obtain at least one extract which contains a mixture of antioxidants; performing thin-layer chromatography on the extract(s) to get a chemical profile; and determining the antioxidant activity profile by reacting the thin-layer chromatography plate(s) with a free radical containing reagent.

In a preferred embodiment, the method involves extracting the sample with a polar solvent, a non-polar solvent and a semi-polar solvent to obtain three extracts which contain three groups of antioxidants; performing thin-layer chromatography on three extracts to get three chemical profiles; and determining the antioxidant activity subprofile by reacting three thin-layer chromatography plates with a free radical containing reagent. The antioxidant activity profile reflects the total antioxidant activity which is composed of antioxidant activities from all individual antioxidants. Identifying the antioxidant activity profile of a sample allows one to determine the change in the overall antioxidant activity of the sample as well as the changes in antioxidant activity of specific individual antioxidant(s).

"Profile" means a record which allows one to determine the amount of each individual antioxidant in the polar, semi-polar or non-polar extracts or any combination of those records. When the profile includes more records from more than one solvent type, "subprofile" refers to the part of the profile which is obtained from one of the polar, semi-polar or non-polar extracts.

"Solvent" means a liquid chemical or a mixture of liquid chemicals which exist without phase separation. The polarity of the solvent (polar, semi-polar or non-polar) refers the overall polarity of the combination of chemicals. For example, an aqueous methanol mixture is considered polar. Whereas some mixtures of methanol and ethyl acetate are semi-polar. Thus, a specific liquid chemical may be used in more than one solvent type. Each solvent is preferably composed of one or more chemicals with similar polarity.

Suitable samples useful in accordance with the present invention include any natural product derived from whole or parts of plants, algae, bacteria, fungi, and animals, such as tissue and blood products from mammals (including human). Preferred plants include herbs; fruits, including especially acerola cherries and plums; vegetables, including especially alfalfa, brassica, legume, watercress, celery and carrot; etc. Concentrates of the above natural products can also be used. Alternatively, products including food supplements, such as vitamins, can also be used.

Extracting The Sample

In accordance with the invention, the sample is extracted with at least one polar solvent, non-polar solvent, or semi-polar solvent. In a preferred embodiment, the sample is extracted with one polar solvent, one non-polar solvent, and one semi-polar solvent.

Polar solvents dissolve polar components of natural products such as vitamin C. Non-polar solvents dissolve non-polar components of natural products such as vitamin E and β-carotene. Semi-polar solvents dissolve other soluble components which are not soluble in polar or non-polar solvents such as α-lipoic acid. It should be understood that some portions of the natural product will not be dissolved in any of these solvents. The remaining portion can be removed from the sample by any conventional technique, for example by centrifugation.

A suitable polar solvent in accordance with the present invention can be composed of water, methanol, isopropanol and acetonitrile or a mixture thereof. A suitable non-polar solvent can include hexane, isooctane, carbon tetrachloride, chloroform, methylene chloride and the like or a mixture thereof. A suitable semi-polar solvent will dissolve and extract semi-polar antioxidants not extracted by polar or non-polar solvents. A suitable semi-polar solvent can includes chloroform, methylene chloride, tetrahydrofuran, ethyl ether, ethyl acetate, acetone, acetonitrile, methanol and the like or mixtures thereof.

Following extractions, the extracts can be concentrated, for example by air drying, rotary evaporation under reduced pressure etc.

Performing Thin-Layer Chromatography On The Extract

Following extractions, the extracts can be chromatographed using either thin layer chromatography (TLC) plates or preparatory plates. TLC and preparatory plates can be obtained commercially from Whatman (Maidstone, Kent, England) or Alltech (Deerfield, Ill.).

The conditions used to develop the chromatographic plates vary according to the extraction conditions.

Determining The Amount and Species Of Chemicals With Antioxidant Activity

The presence of chemicals with antioxidant activity can be assessed by spraying the chromatographic plates with a methanol or a similar volatile solvent with a various amount of a free radical containing agent such as 1,1-diphenyl-2-pycrylhydrazyl (DPPH). DPPH reacts directly with antioxidant(s) after the volatile solvent evaporated to the air in the hood. DPPH undergoes a color change from purple, light purple or red (depends on the amount of DPPH used) to yellow, light yellow or white (the intensity depends on the amount of antioxidant(s) present). If there are no antioxidants, the color of purple, light purple or red will not change. By comparing to the known amount of antioxidant (s), the amount and identity of each individual antioxidant and corresponding activity in a sample can be quantitatively measured by machines such as Camag Reprostar 3 with Camag TLC Scanner 3 (Muttenz, Switzerland).

Optional Comparisons

The antioxidant activity subfiles or profile can be compared against known antioxidants to determine the presence of known antioxidants or to eliminate the re-identification of previously known antioxidants.

The antioxidant activity subfiles or profile can also be compared against that from other samples to determine the relative amounts of individual antioxidants in the samples.

The antioxidant activity subfiles or profile can also be compared against extracts containing known amounts of antioxidants of standards in order to determine, either qualitatively or quantitatively, the amount of antioxidants in the sample.

Alternatively, the antioxidant activity subfiles or profile can be compared against that of control samples (negative controls) to determine the presence of interfering substances generated by the assay procedures.

Optionally Identifying chemicals with Antioxidant Behavior

Compounds identified by the chromatographic means can be isolated and characterized. Ideally, material is developed on preparatory chromatographic plates, a portion of the plate is reacted to the free radical containing reagent to reveal areas containing antioxidant activity, corresponding areas containing antioxidant activity but not reacting to the reagent on the remaining portion of the plate are collected.

The material can be washed off the silica and characterized using known means, including NMR, IR, mass spectroscopy, crystallography, etc. Alternatively, the material can be used as a standard to obtain more compound using scaled up procedures (i.e., liquid chromatography, HPLC, etc.).

Optionally, Determining The Effect Of Time On Antioxidant

The effect of the passage of time on the antioxidant activity of a sample can be monitored by repeating the above steps over time on aliquots of the same sample.

EXAMPLES

1. Extraction

Two daily doses of DOUBLE X® (Amway Corp., Ada, Mich.) and CENTRUM® (a multivitamin made by American Cyanamid Company, Pearl River, N.Y.) were ground into powder and added to a flask containing 50 ml 40% methanol in water and 50 ml hexane. The mixture was homogenized. The upper hexane fraction was concentrated at 30° C. under reduced pressure. The concentrated material was dissolved in 2 ml solvent of hexane:ethyl acetate (3:1). This was the non-polar fraction.

The lower methanol water suspension was centrifuged at 10,000 rpm for 10 min. The supernatant was concentrated at 45° C. under reduced pressure or freeze dried. The concentrated material was dissolved in 2 ml methanol. This was the polar fraction. The precipitate after the centrifugation was further extracted with a mixture of methanol, acetonitrile and ethyl acetate in a ratio of 35:30:35. The suspension was centrifuged at 10,000 rpm for 10 min. The supernatant was concentrated at 40° C. under reduced pressure. The concentrated material was dissolved in 2 ml methanol:ethyl acetate (1:1). This was the semi-polar fraction.

2. Spotting

Three fractions of non-polar, polar and semi-polar properties were spotted on three WHATMAN PE SIL G/UV® silica gel plates separately by hand or a machine such as Camag Automatic Sampler III (Muttenz, Switzerland). The amount and the width of the spotting depend on the concentration of each antioxidants to be detected. Multi-level spotting technique was used to find the best concentration for antioxidants of interest. The spot was air dried in the hood within 2 minutes.

3. Separation of Chemicals

Three plates spotted with different fractions were separately developed under different conditions. In this example, non-polar fraction was run in a container with solvent of hexane:ethyl acetate (3:1). Polar fraction plate was run in the solvent of water, 95% ethanol, 25% ammonium hydroxide (10:78:12). The semi-polar fraction plate was run in the solvent of acetonitrile:methanol:water (35:30:35). The developed plates were taken out and dried in the hood within four minutes.

4. Antioxidant Activity Assay

TLC plates with separated chemical profiles were sprayed with DPPH (20–2000 mm) in methanol. DPPH is a free radical agent which has an intense purple color. When the free radical reacts to an antioxidant, its free radical property is lost due to chain breakage and its color changes to light yellow. Thus, antioxidants appear as yellow bands on a light purple background. Rf values for each band were calculated and photographs were taken.

Results

I) Non-polar fraction

CENTRUM® had one major band with Rf of 0.8, two faint bands of Rf 0.6 and 0.7. DOUBLE X® had 10 bands with Rfs of 0.1, 0.23, 0.47, 0.53, 0.6, 0.63, 0.7, 0.8, 0.9, and 0.94. The band corresponding to Rf 0.6 was tocopherol salt (vitamin E). The bands with Rfs of 0.9 and 0.94 in DOUBLE X® were cis- and trans-$\beta$-carotene, respectively.

II) Polar fraction

Both DOUBLE X® and (CENTRUM® had the same two antioxidants with Rf of 0.7 (vitamin C) and 0.73.

III) Semi-polar fraction

Both DOUBLE X® and CENTRUM® had the same three antioxidants with Rf of 0.8, 0.85 and 0.9. Standards can be used to identify each antioxidants and to quantitate the amount by the intensity measured by a machine such as CAMAG (Muttenz, Switzerland).

Any bands which do not correspond to known antioxidants can be isolated, purified and identified by GC-MS, GC-MS, HPLC, LC-MS, etc.

The invention being thus described, it will be obvious that the same may be varied in many ways. Such variations are not to be regarded as a departure from the spirit and scope of the invention, and all such modifications as would e obvious to one skilled in the art are intended to be included within the scope of the following claims.

What is claimed is:

1. A method of determining the antioxidant activity profile of a sample comprising the steps of:

extracting the sample with a polar solvent, a non-polar solvent and a semi-polar solvent to obtain extracts;

chromatographing the extracts on one or more chromatography plate(s) to get a chemical profile;

determining the presence of antioxidants in the chemical profile by contacting an oxidizing agent that contains a free radical with the chromatography plate(s), wherein the antioxidant activity profile of the sample is represented by a set of bands on the chromatography plate (s); and comparing the antioxidant activity profile obtained from the determining step to an antioxidant activity profile obtained from known standards.

2. The method of claim 1, wherein said sample is a natural product.

3. The method of claim 2, wherein said sample is derived from a plant, algae or bacteria.

4. The method of claim 1, wherein said polar solvent is selected from the group consisting of water, methanol, isopropanol and acetonitrile or a mixture thereof.

5. The method of claim 1, wherein said semi-polar solvent is selected from the group consisting of chloroform, methylene chloride, tetrahydrofuran, ethyl ether, ethyl acetate, acetone, acetonitrile, and methanol or mixtures thereof.

6. The method of claim 1, wherein said non-polar solvent is selected from the group consisting of hexane, isooctane, carbon tetrachloride, chloroform, and methylene chloride or a mixture thereof.

7. The method of claim 1, wherein the extracting is performed on the same sample in series.

8. The method of claim 1, wherein the extracting is performed on more than one aliquot of the same sample in parallel.

9. The method of claim 1, wherein said chromatographing is performed by thin layer chromatography.

10. The method of claim 1, wherein said free radical containing reagent is 1,1-diphenyl-2-picrylhydrazyl.

11. A method of determining the antioxidant activity profile of a sample comprising the steps of:

extracting the sample with a polar solvent, a non-polar solvent and a semi-polar solvent to obtain extracts; wherein the polar solvent is selected from the group consisting of water, methanol, isopropanol, acetonitrile and mixtures thereof; the non-polar solvent is selected from the group consisting of hexane, isooctane, carbon tetrachloride, chloroform, methylene chloride and mixtures thereof; and the semi-polar solvent is selected from the group consisting of chloroform, methylene chloride, tetrahydrofuran, ethyl ether, ethyl acetate, acetone, acetonitrile, methanol and mixtures thereof;

chromatographing each of the polar, non-polar, and semi-polar extracts on one or more chromatography plate(s) to obtain a chemical profile for each extract;

determining the presence of antioxidants in each chemical profile by contacting an oxidizing agent that contains a free radical with the chromatography plate(s), wherein the antioxidant activity profile of the sample is represented by sets of bands on the chromatography plate(s); and comparing the antioxidant activity profile obtained from the determining step to an antioxidant activity profile obtained from known standards.

* * * * *